US00PP20368P2

(12) United States Plant Patent
Bett

(10) Patent No.: US PP20,368 P2
(45) Date of Patent: Sep. 29, 2009

(54) ***SEDUM* PLANT NAMED 'ELSIE'S GOLD'**

(50) Latin Name: *Sedum spectabile*
Varietal Denomination: ELSIE'S GOLD

(76) Inventor: Robert Bett, 82 Trig Road, Whenuapai, Auckland (NZ)

( * ) Notice: Subject to any disclaimer, the term of this patent is extended or adjusted under 35 U.S.C. 154(b) by 0 days.

(21) Appl. No.: 12/220,870

(22) Filed: Jul. 28, 2008

(51) Int. Cl.
*A01H 5/00* (2006.01)

(52) U.S. Cl. ..... Plt./479

(58) Field of Classification Search ..... Plt./479
See application file for complete search history.

*Primary Examiner*—Annette H Para

(57) ABSTRACT

A new and distinct cultivar of *Sedum* named 'ELSIE'S GOLD' that is characterized by clump forming habit, thick variegated green and cream-white foliage, and pink flowers. In combination these traits set 'ELSIE'S GOLD' apart from all other existing varieties of *Sedum* known to the inventor.

4 Drawing Sheets

Genus: *Sedum.*
Species: *spectabile.*
Denomination: 'ELSIE'S GOLD'.

BACKGROUND OF THE INVENTION

This application claims the benefit of priority under 35 U.S.C. 119(f) of the earlier-filed application for New Zealand Plant Breeders Rights, Application Number HOM239 filed Aug. 6, 2007.

The present invention relates to a new variety of stonecrop grown as an ornamental for use in containers and for growing in the garden border or landscape. The new invention from the family Crassulaceae is known botanically as *Sedum spectabile* and will be referred to hereinafter as 'ELSIE'S GOLD'.

'ELSIE'S GOLD' was discovered as a naturally occurring branch sport of *Sedum* 'Herbstfreude'. The sole parent is an individual *Sedum* 'Herbstfreude' (unpatented) which is also known in commerce as 'Autumn Joy'. The inventor discovered 'ELSIE'S GOLD' in April 2003 at the inventor's nursery in Whenapai, Auckland, New Zealand. Selection was based on the criterion of unique variegated foliage.

'ELSIE'S GOLD' exhibits clumping habit, striking variegated leaves that are silver-green with bold yellow-gold margins fading to soft cream-white by autumn, and flowers that open pale shell-pink in color, aging to a deep saturated pink. 'ELSIE'S GOLD' is 0.3 m. in height and 0.3 m. in width the first year, reaching 0.45 m. in height and 0.45 m. in width at maturity. Cultural needs include free-draining soil, full sun, and minimal water. 'ELSIE'S GOLD' is susceptible to snails, slugs, and mildew. Spraying is recommended in areas of high humidity to prevent mildew, and use of snail bait is recommended to prevent damage from snails and slugs. 'ELSIE'S GOLD' is hardy in USDA Zone 6.

'ELSIES GOLD' is unique and distinguishable from any other *Sedum* known to the inventor. The closest comparison plant is *Sedum* 'Autumn Joy'. 'ELSIE'S GOLD' is distinguishable from the comparison plant by variegated foliage, and flower color. The foliage on 'Autumn Joy' is solid green in color, and the flowers open dark pink aging to brick-red. Foliage on 'ELSIE'S GOLD' is variegated, and the flower opens pale pink.

The first asexual reproduction of 'ELSIE'S GOLD' was accomplished by the inventor in Auckland, New Zealand in December 2003 using tip cuttings. Since the first asexual propagation, and under careful observation 'ELSIE'S GOLD' has been determined fixed, stable and to reproduce true to type in subsequent generations of asexual propagation.

SUMMARY OF THE INVENTION

The following traits have been repeatedly observed and represent the distinguishing characteristics of the new *Sedum* cultivar named 'ELSIE'S GOLD'. These traits in combination distinguish 'ELSIE'S GOLD' from all other existing varieties of *Sedum* known to the inventor. 'ELSIE'S GOLD' has not been tested under all possible conditions. Phenotypic differences may be observed with variations in environmental, climatic, and cultural conditions without however any variance in genotype.

1. 'ELSIE'S GOLD' exhibits clump forming habit.
2. 'ELSIE'S GOLD' exhibits thick silver-green leaves with bold yellow-gold margins fading to soft cream-white.
3. 'ELSIE'S GOLD' exhibits flowers that open pale shell-pink aging to saturated pink.
4. 'ELSIE'S GOLD' is 0.45 m. in height and 0.45 m. in width at maturity.
5. 'ELSIE'S GOLD' blooms late summer to fall.
6. 'ELSIE'S GOLD' is hardy in USDA Zone 6.

BRIEF DESCRIPTION OF THE DRAWINGS

The accompanying color drawings illustrate the overall appearance of the new *Sedum* cultivar named 'ELSIE'S GOLD' showing color as true as is reasonably possible to obtain in color reproductions of this type. Color in the drawings may differ from color values cited in the detailed botanical description, which accurately describe the actual color of the new variety named 'ELSIE'S GOLD'.

Figure 1:
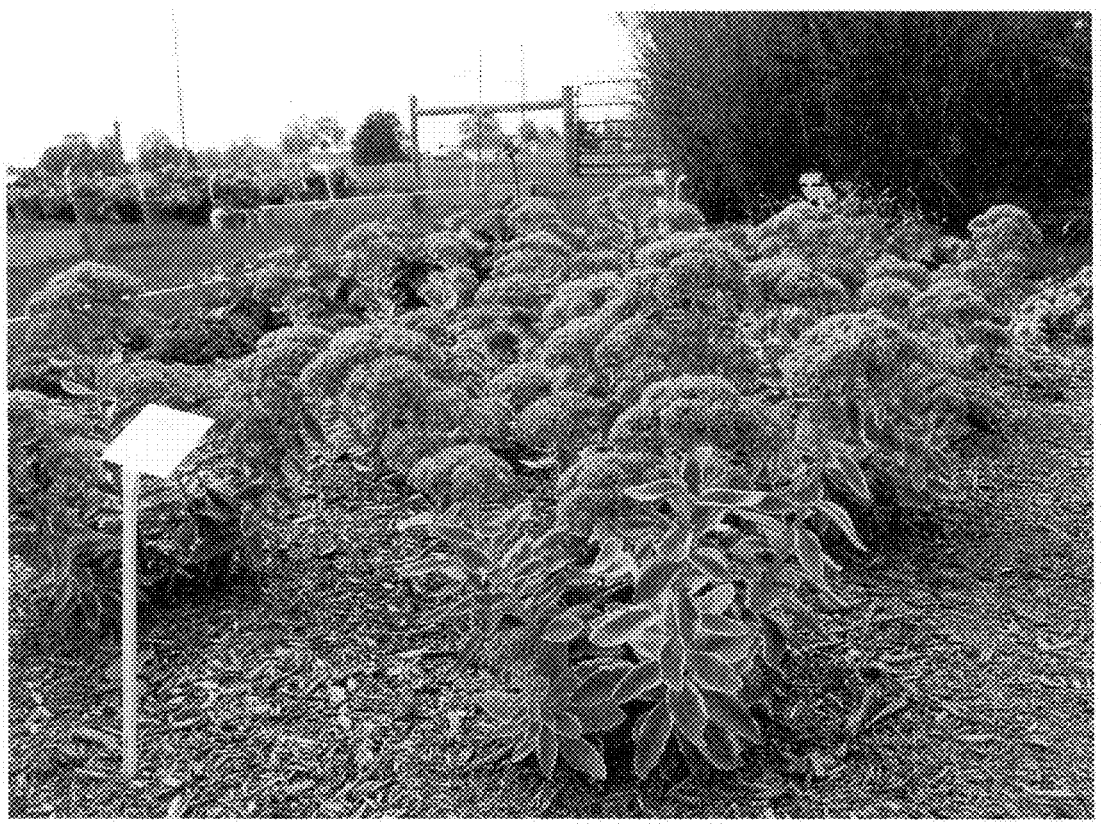
FIG. 1 depicts a block planting of 'ELSIE'S GOLD'.
Figure 2:
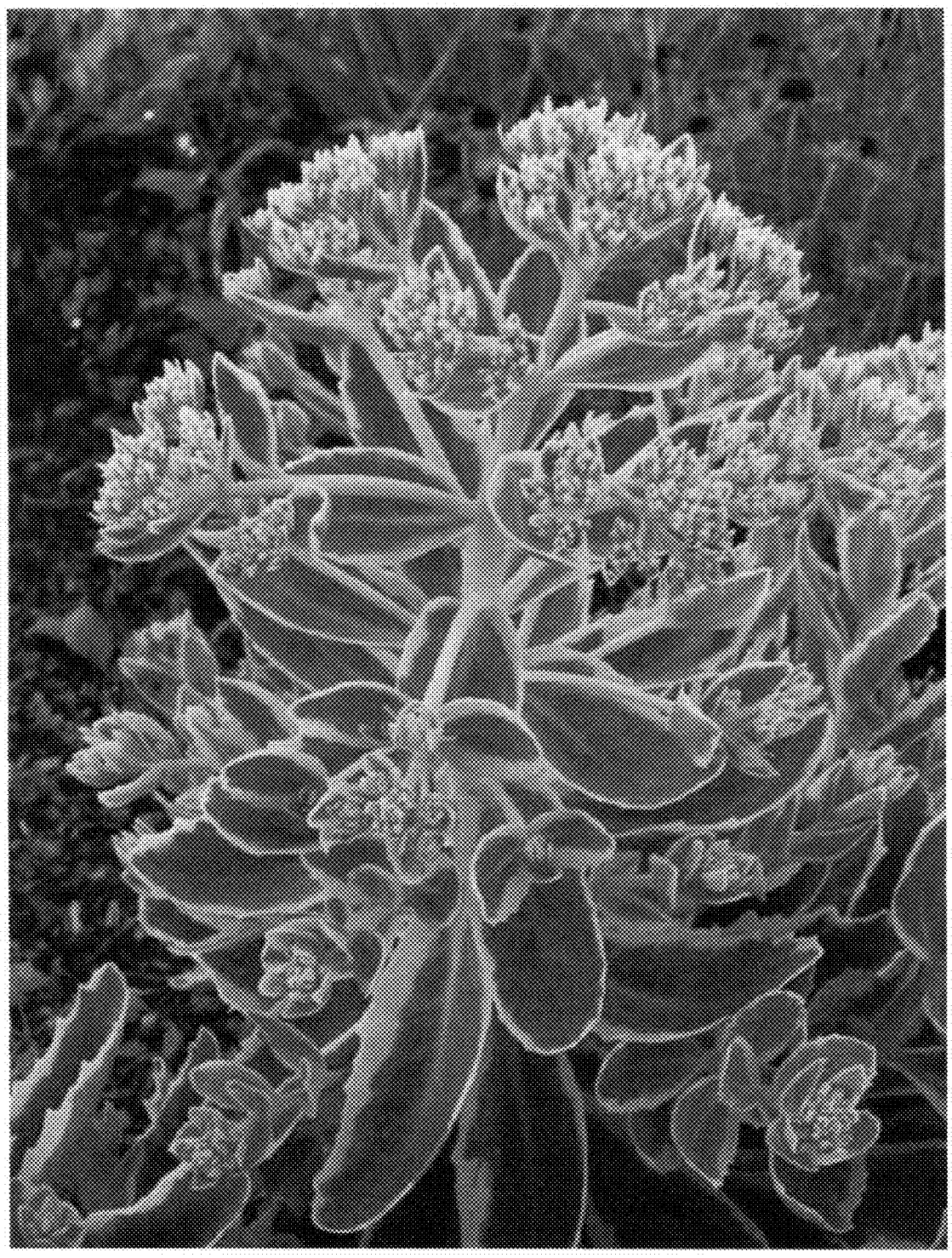
FIG. 2 depicts a close-up view of the foliage and newly-emerging inflorescence.
Figure 3:
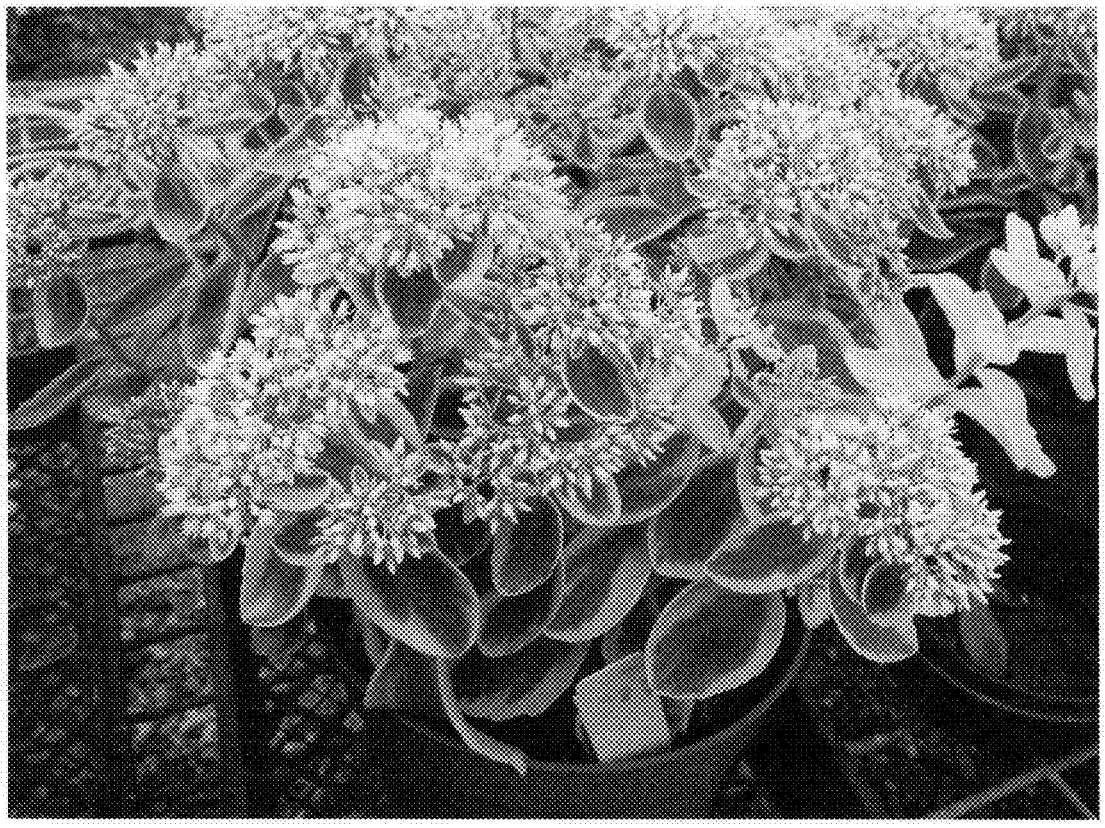
FIG. 3 depicts a close-up of the foliage and the inflorescence in bud and first opening.
Figure 4:
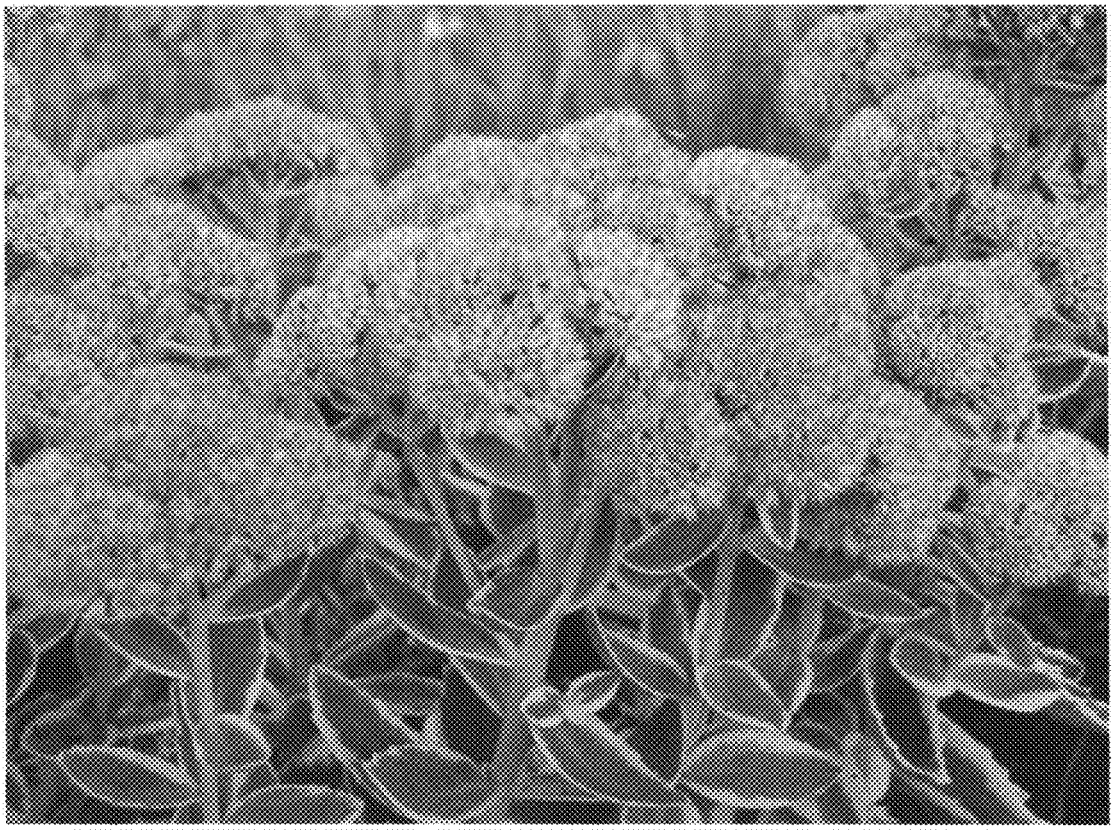
FIG. 4 depicts a close-up of the mature inflorescence.

Drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Sedum* cultivar named 'ELSIE'S GOLD'. Observations, measurements, values and comparisons were collected in Arroyo Grande, Calif., from 18-month-old plants grown out-of-doors in 2-litre containers. Color determinations are made in accordance with the 2002 Royal Horticultural Society Colour Chart from London, England, except where general color terms of ordinary dictionary significance are used. The growing requirements of the new variety 'ELSIE'S GOLD' are similar to the species.

Botanical classification: *Sedum spectabile* 'ELSIE'S GOLD'.
Family: Crassulaceae.
Genus: *Sedum*.
Species: *spectabile*.
Denomination: 'ELSIE'S GOLD'.
Common name: Stonecrop.
Habit: Clump forming.
Commercial category: Succulent.
Use: Container and border.
Suggested commercial container size: 2-litre container.
Parentage: *Sedum spectabile* 'ELSIE'S GOLD' was discovered as a branch sport of *Sedum* 'Autumn Joy' (unpatented).
Propagation method: Tip cuttings, and tissue culture.
Rooting system: Fine and fibrous.
Vigor: Moderate.
Crop time (range): 8–16 weeks from a cutting to a 5 cm. pot and 16–24 weeks from a tip cutting to a finished 2-litre container plant.
Temperature (range): The recommended air temperature is 20–21° Centigrade.
Plant dimensions (first year): 0.3 m. in height and 0.3 m. in width.
Plant dimensions (at maturity): 0.45 m. in height and 0.45 m. in width.
Cultural requirements: Grow in free-draining soil and full sun, with minimal water.
Pest and disease resistance: None known to the inventor.
Pest and disease susceptibility: Mildew, snails and slugs/similar to other Kniphofia.
Hardiness: USDA Zone 6.
Special considerations: Spray in humid areas to prevent mildew.
Stem:
- *Branching habit.*—Rosette.
- *Trunk height.*—8–10 cm.
- *Trunk diameter.*—3.75 cm.
- *Trunk color.*—145A.
- *Stem surface.*—Glabrous.
- *Stem length.*—20–22 cm.
- *Stem diameter.*—1.10 cm.
- *Stem color.*—145A.
- *Stem strength.*—Strong.
- *Stem appearance.*—Semi-glossy.
- *Stem quantity* (*average*).—16 per 1-litre container.
- *Leaf scars.*—Present.
- *Leaf scar shape.*—Elliptic.
- *Leaf scar width.*—0.60 cm.
- *Leaf scar height.*—8–10 cm.
- *Leaf scar quantity* (*average*).—15 per stem.
- *Leaf scar color.*—163B.
- *Internode.*—0.50 cm.

Foliage:
- *Type.*—Winter deciduous.
- *Leaf quantity* (*range*).—38–40 per stem.
- *Leaf attachment.*—Sessile.
- *Leaf arrangement.*—Alternate.
- *Leaf texture.*—Rubbery and thick.
- *Leaf division.*—Simple.
- *Leaf margin.*—Dentate.
- *Leaf surface* (*abaxial and adaxial*).—Glabrous.
- *Leaf shape.*—Elongated oval.
- *Leaf length* (*average*).—8 cm.
- *Leaf width* (*average*).—4 cm.
- *Leaf color* (*both surfaces*).—N144A, 189A, 158B are all present.
- *Leaf apex* (*range*).—Acute to rounded.
- *Leaf base.*—Truncate.
- *Venation.*—Pinnate.
- *Vein color* (*abaxial and adaxial surfaces*).—N144A.
- *Leaf fragrance.*—None observed.

Inflorescence:
- *Type.*—Terminal cyme.
- *Blooming season.*—Late summer to fall.
- *Inflorescence quantity* (*average*).—12 per peduncle.
- *Inflorescence dimensions* (*average*).—2 cm. in length and 4 cm. in width.
- *Inflorescence quantity* (*average*).—400 per terminal inflorescence.
- *Flower aspect.*—Facing upward.
- *Bud shape.*—Ovoid.
- *Bud surface.*—Glabrous.
- *Bud apex.*—Rounded.
- *Bud base.*—Rounded.
- *Bud color.*—138B.
- *Bud quantity* (*average*).—400 per terminal inflorescence.
- *Bud dimensions.*—3 mm. in length and 2.50 cm. in width.
- *Pedicel shape.*—Subcylindrical.
- *Pedicel color.*—138B.
- *Pedicel surface.*—Glabrous.
- *Pedicel dimensions.*—2 mm. in length and <0.50 mm. in width.
- *Flower fragrance.*—None observed.

Reproductive organs:
- *Stamen quantity.*—5 in number.
- *Ovary position.*—Superior.
- *Ovary shape.*—Ovoid.
- *Ovary dimensions.*—0.50 cm. in height and 0.25 cm. in diameter.
- *Ovary color.*—144D.

What is claimed is:

1. A new and distinct cultivar of *Sedum* plant named 'ELSIE'S GOLD' as described and illustrated herein.

* * * * *